(12) United States Patent
Rossi

(10) Patent No.: US 9,302,114 B2
(45) Date of Patent: Apr. 5, 2016

(54) ENERGY-RELEASING CARBON NANOTUBE TRANSPONDER AND METHOD OF USING SAME

(71) Applicant: Rush University Medical Center, Chicago, IL (US)

(72) Inventor: Marvin A. Rossi, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 14/317,935

(22) Filed: Jun. 27, 2014

(65) Prior Publication Data

US 2014/0309715 A1    Oct. 16, 2014

Related U.S. Application Data

(60) Division of application No. 13/421,297, filed on Mar. 15, 2012, now Pat. No. 8,788,033, which is a continuation-in-part of application No. PCT/US2010/048956, filed on Sep. 15, 2010.

(60) Provisional application No. 61/242,691, filed on Sep. 15, 2009.

(51) Int. Cl.
*A61N 1/365* (2006.01)
*A61N 1/362* (2006.01)
(Continued)

(52) U.S. Cl.
CPC .............. *A61N 1/37205* (2013.01); *A61N 1/00* (2013.01); *A61N 1/205* (2013.01); *A61N 1/362* (2013.01); *B82Y 30/00* (2013.01); *A61N 1/325* (2013.01); *A61N 1/327* (2013.01)

(58) Field of Classification Search
CPC ....... A61N 1/205; A61N 1/326; A61N 1/325; A61N 1/00; A61N 1/37205; A61N 1/327; A61N 1/362; B82Y 5/00; B82Y 30/00; Y10S 977/904

USPC ............................................................ 607/2
See application file for complete search history.

(56) References Cited

U.S. PATENT DOCUMENTS

2004/0142172 A1    7/2004   Sugiyama et al.
2005/0245857 A1   11/2005   Pizzi et al.
(Continued)

OTHER PUBLICATIONS

Okumoto et al. "Detection of glutamate release from neurons by genetically encoded surface-displayed FRET nanosensors", Proc Natl Acad Sci U S A. Jun. 14, 2005; 102(24):8740-5.*

(Continued)

*Primary Examiner* — Carl H Layno
*Assistant Examiner* — Erin M Piateski
(74) *Attorney, Agent, or Firm* — Brinks Gilson & Lione

(57) ABSTRACT

An energy-releasing carbon nanotube transponder comprising a nanocapacitor connected to at least one carbon nanotube and method of using same are described. An adjustable amount of electric energy is stored within the nanocapacitor so that the energy-releasing carbon nanotube transponder delivers either a biologically destructive or a biologically non-destructive electrical charge to target cells in response to biological, chemical or electrical stimuli. An optional biocompatible coating onto the outer surface of the carbon nanotube transponder improves cellular targeting, cellular binding or body tolerance towards the carbon nanotube transponder. Optionally, a molecular label attached to at least one carbon nanotube allows for in vivo tracking of the carbon nanotube transponder. The targeted release of electric energy from the carbon nanotube transponder can, for example, destroy cancer cells in cancer patients, or control the flux of electric wave within a cellular tissue to treat cardiac and/or epileptic patients.

22 Claims, 1 Drawing Sheet

(51) Int. Cl.
| | |
|---|---|
| A61N 1/378 | (2006.01) |
| B82Y 5/00 | (2011.01) |
| A61N 1/372 | (2006.01) |
| A61N 1/00 | (2006.01) |
| A61N 1/20 | (2006.01) |
| B82Y 30/00 | (2011.01) |
| A61N 1/32 | (2006.01) |

(56) References Cited

U.S. PATENT DOCUMENTS

| | | | |
|---|---|---|---|
| 2006/0184092 A1 | 8/2006 | Atanasoska et al. | |
| 2007/0060815 A1* | 3/2007 | Martin et al. | 600/372 |
| 2007/0156082 A1 | 7/2007 | Scherman | |
| 2007/0281657 A1* | 12/2007 | Brommer et al. | 455/334 |
| 2008/0274202 A1 | 11/2008 | Kraig et al. | |
| 2008/0302660 A1 | 12/2008 | Kahn et al. | |
| 2008/0319506 A1 | 12/2008 | Caulier | |
| 2009/0022655 A1* | 1/2009 | Buzatu et al. | 424/1.29 |

OTHER PUBLICATIONS

Akhtari M, et al.; "Electrical conductivities of the freshly excised cerebral cortex in epilepsy surgery patients; correlation with pathology, seizure duration, and diffusion tensor imaging"; Brain Topogr. 2006 Summer; 18(4):281-90.
Allen et al.; Nano-engineering block copolymer aggregates for drug delivery, Colloids Surf B: Biointerfaces 16:3-27 (1999).
Azamian BR, et al.; Bioelectrochemical single-walled carbon nanotubes. JAm Chem Soc. Oct. 30, 2002;124 (43):12664-5.
Baddour, CE et al.; Carbon Nanotube Synthesis: A Review; International Journal of Chemical Reactor Engineering, vol. 3, Issue 1; 1542-6580; DOI: 10.2202/1542-6580.1279; Aug. 2005; Abstract.
Balasubramanian K, et al; Chemically functionalized carbon nanotubes. Small. Feb. 2005;1(2):18O-92.
Benabid AL et al.; "Deep brain stimulation of the subthalamic nucleus for the treatment of Parkinson's disease"; Lancet Neurol. Jan. 2009;8(1):67-81.
Beurrier C, et al.; High-frequency stimulation produces a transient blockade of voltage-gated currents in subthalamic neurons. J Neurophysiol. Apr. 2001;85(4):1351-6.
Butson CR, et al.; Patient-specific analysis of the volume of tissue activated during deep brain stimulation. Neuroimage. Jan. 15, 2007;34(2):661-70.
Butson CR, et al.; Role of electrode design on the volume of tissue activated during deep brain stimulation. J Neura Eng. Mar. 2006;3(1):1-8.
Caput D, et al.; Cloning and characterization of a specific interleukin (IL)-13 binding protein structurally related to the IL-5 receptor alpha chain. J Biol Chem. Jul. 12, 1996;271(28): 16921-6.
Chen J, et al.; Functionalized single-walled carbon nanotubes as rationally designed vehicles for tumor-targeted drug delivery. J Am Chem Soc. Dec. 10, 2008;130(49):16778-85.
Chen RJ, et al. An investigation of the mechanisms of electronic sensing of protein adsorption on carbon nanotube devices. J Am Chem Soc. Feb. 11, 2004; 126(5): 1563-8.
Debinski W, et al.; Molecular expression analysis of restrictive receptor for interleukin 13, a brain tumor-associated cancer/testis antigen. Mol Med. May 2000;6(5):440-9.
Deep-Brain Stimulation for Parkinson's Disease Study Group. Deep-brain stimulation of the subthalamic nucleus or the pars interna of the globus pallidus in Parkinson's disease. N Engl J Med. Sep. 27, 2001;345(13):956-63.
Dostrovsky JO, et al.; Microstimulation-induced inhibition of neuronal firing in human globus pallidus. J Neurophysiol. Jul. 2000;84(1):570-4.
Fisher R, et al.; "Electrical stimulation of the anterior nucleus of thalamus for treatment of refractory epilepsy"; Epilepsia. May 2010;51(5):899-908.

Fukuda M, et al.; Networks mediating the clinical effects of pallidal brain stimulation for Parkinson's disease: a PET study of resting-state glucose metabolism. Brain. Aug. 2001;124(Pt 8):1601-9.
Gannon CJ, et al.; Carbon nanotube-enhanced thermal destruction of cancer cells in a noninvasive radiofrequency field. Cancer. Dec. 15, 2007;110(12):2654-65.
Gruner G. Carbon nanotube transistors for biosensing applications. Anal Bioanal Chem. Jan. 2006;384(2):322-35.
Husain SR, et al.; Interleukin-13 receptor-directed cytotoxin for malignant glioma therapy: from bench to bedside. J Neurooncol. Oct. 2003;65(1):37-48.
Iijima; Helical microtubules of graphitic carbon, Nature 354:56-58 (1991).
Ishikawa FN, et al.; Label-free, electrical detection of the SARS virus N-protein with nanowire biosensors utilizing antibody mimics as capture probes. ACS Nano. May 26, 2009a;3(5):1219-24.
Ishikawa FN, et al.; Rapid and label-free cell detection by metal-cluster-decorated carbon nanotube biosensors. Biosens Bioelectron. Jun. 15, 2009b;24(10):2967-72.
Ji SR, et al.; Carbon nanotubes in cancer diagnosis and therapy. Biochim Biophys Acta. Aug. 2010;1806(1):29-35.
Kakinuma K, et al.; Targeting chemotherapy for malignant brain tumor using thermosensitive liposome and localized hyperthermia. J Neurosurg. Feb. 1996;84(2):180-4.
Kam NW, et al.; Carbon nanotubes as multifunctional biological transporters and near-infrared agents for selective cancer cell destruction. Proc Nat! Acad Sci USA. Aug. 16, 2005; 1 02(33): 11600-5.
Khetpal et al.; Polyfunctionalized single-walled carbon nanotubes as a versatile platform for cancer detection and targeted dual therapy. Intel STS Abstract (2009).
Kawakami M, et al.; Intratumor administration of interleukin 13 receptor-targeted cytotoxin induces apoptotic cell death in human malignant glioma tumor xenografis. Mol Cancer Ther. Oct. 2002; 1 (12):999-1007.
Kiss ZH, et al.; Functional and Stereotactic Section of the Canadian Neurosurgical Society; Canadian Movement Disorders Group. The Canadian multicentre study of deep brain stimulation for cervical dystonia. Brain. Nov. 2007; 130(Pt 11 ):2879-86.
Lee et al.; Carbon nanotube-based labels for highly sensitive colorimetric and aggregation-based visual detection of nucleic acids. Nanotechnol.18(45) 455102.1-455102.9 (2007).
Lee W, et al.; Wiring neurons with carbon nanotubes. Front Neuroeng. May 29, 2009;2:8.
Liu Z, et al.; Drug delivery with carbon nanotubes for in vivo cancer treatment. Cancer Res. Aug. 15, 2008;68 (16):6652-60.
Lu et al.; Advances in bloapplications of carbon nanotubes. Adv Materials. 21: 139-152 (2009).
Mckenzie AN, et al.; Interleukin 13, a T-cell-derived cytokine that regulates human monocyte and B-cell function. Proc Natl Acad Sci USA. Apr. 15, 1993;90(8):3735-9.
Minty A, et al.: Interleukin-13 is a new human lymphokine regulating inflammatory and immune responses. Nature. Mar. 18, 1993;362(6417):248-50.
Mintz A, et al.; Molecular targeting with recombinant cytotoxins of interleukin-13 receptor alpha2-expressing glioma. J Neurooncol. Aug.-Sep. 2003;64( 1-2): 117-23.
Miocinovic S, et al.; Computational analysis of subthalamic nucleus and lenticular fasciculus activation during therapeutic deep brain stimulation. J Neurophysiol. Sep. 2006;96(3): 1569-80.
Murad GJ, et al.; Real-time, image-guided, convection-enhanced delivery of interleukin 13 bound to pseudomonas exotoxin. Clin Cancer Res. May 15, 2006;12(10):3145-51.
Nash KT, et al.; Molecular targeting of malignant gliomas with novel multiply-mutated interleukin 13-based cytotoxins. Crit Rev Oncol Hematol. Jul.-Aug. 2001; 39(1-2):87-98.
Okumoto S, et al.; Detection of glutamate release from neurons by genetically encoded surface-displayed FRET nanosensors. Proc Natl Acad Sci USA. Jun. 14, 2005;102(24):8740-5.
Pantarotto D, et al.; Translocation of bioactive peptides across cell membranes by carbon nanotubes. Chem Commun (Camb). Jan. 7, 2004;(1):16-7.

(56) References Cited

OTHER PUBLICATIONS

Panchapakesan et al.: Single-wall carbon nanotubes with adsorbed antibodies detect live breast cancer cells, NanoBiotech 1:353-360 (2005).
Park JH, et al.; Cooperative nanomaterial system to sensitize, target, and treat tumors. Proc Natl Acad Sci USA. Jan. 19, 2010;107(3):981-6.
Ramanathan et al.; Amino-Functionalized Carbon Nanotubes for Binding to Polymers and Biological Systems. Chemistry of Materials, 17:1290-1295 (2005).
Rossi MA, et al.; Predicting white matter targets for direct neurostimulation therapy. Epilepsy Res. Oct. 2010;91 (2-3):176-86.
Rossi, MA, et al.; "Substracted Activated SPECT Validates Depth Lead Placement in White Matter for Responsive Neurostimulation Therapy in Refractory Partial-Onset Epilepsy"; Epilepsia, 49 (suppl. 7):I-498; 2008. Abstract.
Salmenpera TM, et al.; "Postictal diffusion weighted imaging"; Epilepsy Res. Aug. 2006;70(2-3):133-43.
Sampson JH, et al.; PRECISE Trial Investigators. Poor drug distribution as a possible explanation for the results of the PRECISE trial. J Neurosurg. Aug. 2010;113(2):301-9.
Sapra P, et al.; Ligand-targeted liposomal anticancer drugs. Prog Lipid Res. Sep. 2003;42(5):439-62.
Schipper ML, et al.: A pilot toxicology study of single-walled carbon nanotubes in a small sample of mice. Nat Nanotechnol. Apr. 2008;3(4):216-21.
Singh R, et al.; Tissue biodistribution and blood clearance rates of intravenously administered carbon nanotube radiotracers. Proc Natl Acad Sci USA. Feb. 28, 2006; 1 03(9):3357-62.
Teker, Bioconjugated carbon nanotubes for targeting cancer biomarkers, Materials Science Engineering 153 (1-3):83-87 (2008).
Thess A, et al.; Crystalline Ropes of Metallic Carbon Nanotubes. Science. Jul. 26, 1996;273(5274):483-7.
Tuch DS, et al.; Conductivity tensor mapping of the human brain using diffusion tensor MRI. Proc Natl Acad Sci U S A. Sep. 25, 2001;98(20):11697-701.
Urbano FJ, et al.; "Cortical activation patterns evoked by afferent axons stimuli at different frequencies: an in vivo voltage-sensitive dye imaging study"; Thalamus Relat. Syst. 2002;1:371-378.
VanLandingham KE, et al.; "Self-sustaining limbic status epilepticus. II"; Role of hippocampal commissures in metabolic responses. Neurology. Dec. 1991;41(12):1950-7.
Vasques X, et al.; "Stereotactic model of the electrical distribution within the internal globus pallidus during deep brain stimulation"; J Comput Neurosci. Feb. 2009;26(1):109-18.
Velasco F, et al.; "Electrical stimulation for epilepsy: stimulation of hippocampal foci."; Stereotact Funct Neurosurg; 2001; 77(1-4):223-7; downloaded from the internet on Dec. 12, 2013 at http://www.ncbi.nlm.nih.gov/pubmed/12378080?dopt=Abstract; Abstract.
Velasco M, et al.; "Subacute electrical stimulation of the hippocampus blocks intractable temporal lobe seizures and paroxysmal EEG activities"; Epilepsia. Feb. 2000;41(2):158-69.
Vidailhet M, et al.; French Stimulation du Pallidum Interne dans la Dystonie (SPIDY) Study Group. Bilateral deep-brain stimulation of the globus pallidus in primary generalized dystonia. N Engl J Med. Feb. 3, 2005;352(5):459-67.
Von Mal Tzahn G, et al.; Computationally guided photothermal tumor therapy using long-circulating gold nanorod antennas. Cancer Res. May 1, 2009;69(9):3892-900.
WHO Fact Sheet No. 999 (Jan. 2009).
Wu W, et al.; Covalently combining carbon nanotubes with anticancer agent: preparation and antitumor activity. ACS Nano. Sep. 22, 2009;3(9):2740-50.
Yang ST, et al.; Long-term accumulation and low toxicity of single-walled carbon nanotubes in intravenously exposed mice. Toxicol Lett. Oct. 1, 2008;181(3):182-9.
Yudasaka et ai, Single-walled nanotube formation by laser ablation using double-targets of carbon and metal, Chern Phys Lett 278: 1 02-1 06 (1997).
Zhou G, et al.; Engineered herpes simplex virus 1 is dependent on IL 13Ralpha 2 receptor for cell entry and independent of glycoprotein D receptor interaction. Proc Natl Acad Sci USA. Nov. 12, 2002;99(23):15124-9.
International Search Report and Written Opinion, mailed on Nov. 1, 2010, for related International Application No. PCT/US20101048956 filed on Sep. 15, 2010.

* cited by examiner

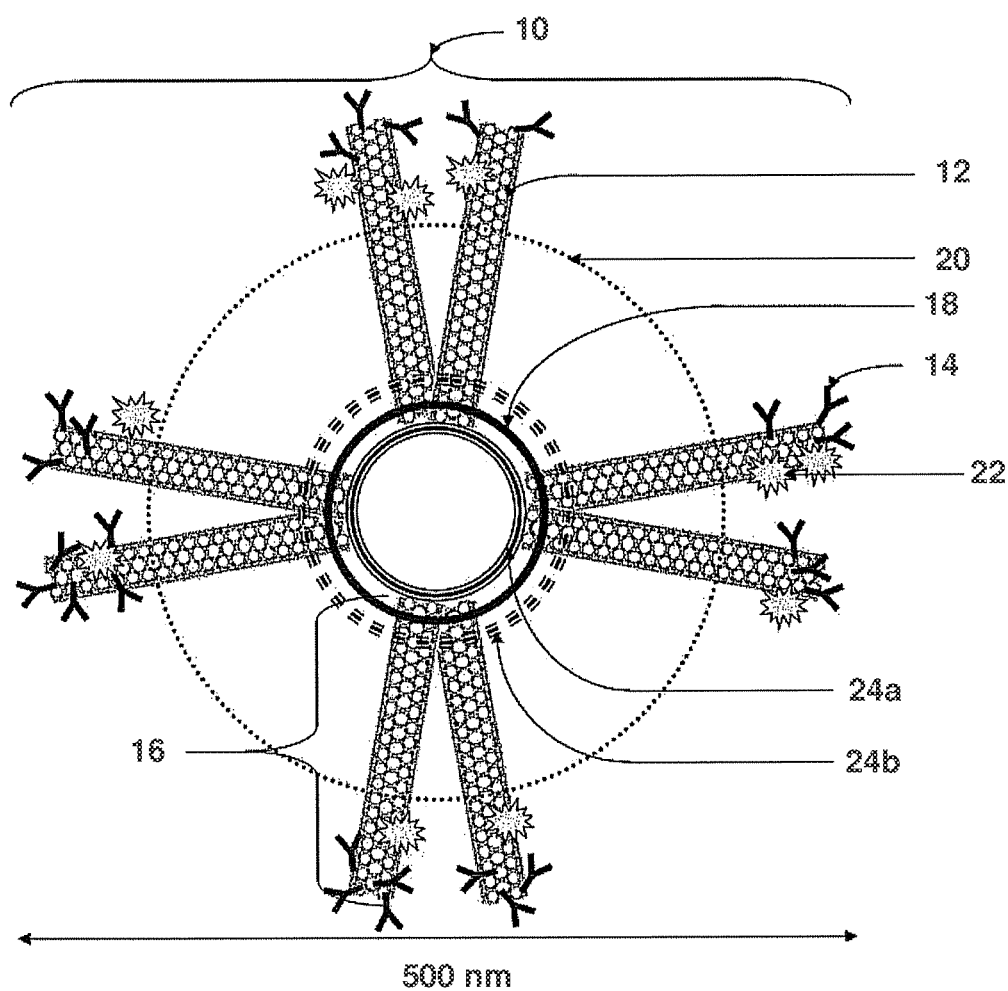

ENERGY-RELEASING CARBON NANOTUBE TRANSPONDER AND METHOD OF USING SAME

This application is a division of U.S. application Ser. No. 13/421,297 filed Mar. 15, 2012, now U.S. Pat. No. 8,788,033, which is a continuation-in-part of International Application No. PCT/US2010/048956 filed Sep. 15, 2010, which claims the priority benefit under 35 U.S.C. section 119 of U.S. Provisional Patent Application 61242691 filed Sep. 15th, 2009, all of which are incorporated by reference in their entirety.

FIELD OF THE INVENTION

This invention relates generally to nanotechnology, and more particularly to a new device, electrically charged and termed an Energy-Releasing Carbon Nanotube Transponder, and to methods of using the charged Energy-Releasing Carbon Nanotube Transponder to treat human and non-human afflictions by delivering at least one biologically destructive electric charge or at least one biologically non-destructive electric charge directly within a tissue to be treated.

BACKGROUND OF THE INVENTION

The present invention relates to nanoscale electromechanical devices and their use in medical therapy. More particularly, the present invention relates to an energy-releasing carbon nanotube transponder that can be fabricated from a plurality of carbon nanotubes optionally attached to at least one biomolecule ligand and connected to a nanocapacitor. Such an energy-releasing carbon nanotube transponder can be placed in cellular tissue to treat multiple afflictions.

The term "patient" is usually understood as any person who receives medical attention, care, or treatment. However, many afflictions found in human patients can also be found in s for example cancer. The patients of veterinarians are animals. Therefore it should be understood that the invention described in this application can be used to treat humans and animals. Moreover, in this application the term "animal" includes any non-human multicellular, eukaryotic organisms such as for example fish, birds, insects, reptiles, and non-human mammals.

The term "tissue" usually describes an ensemble of cells, not necessarily identical, that together carry out a specific function. For example, organs are formed by the functional grouping together of multiple tissues. However, this invention encompasses the field of nanotechnology, therefore the invention described in this application is so small that it can be used to treat a single cellular entity, for example a single neuron or a single cancer cell. It should be understood, that when the term "tissue" is used in this application, it is meant one or more cells as appropriate for treatment. Moreover, in this application, the term "cell" includes any "cellular entity" and it should not be limited to human and animal cells, for example, the term "cell" in this application encompasses bacterial or even viral entities. For example, cancers are sometimes of viral or bacterial origins, therefore the treatment of cancer, as described in this application, can also include the destruction of the bacterial and/or the viral entities that trigger or promote cancer.

In this application, the term "treatment" should not be limited to a synonym for therapy used to remedy a health problem, but should also be broadened to mean a process of modifying or altering one or more cells.

Cancer is presently one of the most difficult fatal conditions to treat. President Nixon declared "war" on cancer back in 1971, and research for cancer treatments has remained at a high level since then. Cancer is caused by the growth of malignant cells in a patient. Conventional treatments for cancer seek to kill or inhibit the growth of cancer cells, but also kill or inhibit the growth of healthy cells as well. The search for a balance between treating cancer and not killing the patient can often result in unsuccessful cancer treatment. Therefore, there is a need for cancer treatments that better target malignant cells without damaging healthy cells.

In brain cancer, infiltrative primary high-grade neoplastic cells in the central nervous system (CNS) are often resistant to conventional chemotherapeutic and radiation therapies. Chemotherapy and radiation administered both inside the CNS and outside the blood brain barrier often cannot reach densely packed malignant cells even following respective debulking. Moreover, conventional chemotherapeutic agents can have limited efficacy due to factors ranging from systemic toxicity, to impaired drug transport secondary to decreased vascularization of the neoplasm core and P-glycoprotein-mediated drug efflux. These limitations of conventional therapies have inspired investigational nanotechnology approaches to therapy.

Epilepsy is one of the world's oldest recognized conditions. The World Health Organization (WHO) estimates that about 50 million people worldwide suffer from epilepsy. See WHO Fact Sheet No. 999 (January 2009). Epilepsy is caused by sudden, usually brief, electrical discharges in the brain. The symptoms can range from a brief loss of attention to prolonged and severe convulsions.

Epilepsy can be thought of as being like an electrical circuit that has been disturbed and has become unstable. Many patients manage their symptoms with drugs that inhibit the onset of epileptic seizures. However, many individuals are affected by medically intractable epilepsy where surgical options are minimal or non-existent. To address these issues novel treatment approaches are being developed: The delivery of treatment stimulation contingent on detection of the ictal onset (e.g. seizure) at the epileptic source is the next generation of implantable technologies directed toward optimizing containment of epileptic brain circuits. Such technologies are crucial in individuals with medically intractable epilepsy where surgical options are minimal or non-existent. Results emerging from the Food and Drug Administration (FDA)-sponsored investigational neurostimulation trials are promising. However, nearly all patients enrolled in these studies continue to experience breakthrough seizures. Relatively bulky intracranial electrodes are utilized in these studies while the number of electrodes that can be implanted is limited by their size. Moreover, the implantation of a multiplicity of bulky electrode may result in brain tissue damage. Epileptic networks can be complex and may extend well beyond implanted bulky intracranial electrodes. To optimize stimulation of brain tissue without using bulky electrodes, a multiplicity of nanodevices can be utilized to target specific brain cells while minimizing potential brain damage.

The energy-releasing carbon nanotube transponder described in this application has significant implications outside of epilepsy. Such an energy-releasing carbon nanotube transponder can also be used to investigate the brain's ability to record and replay the neural code involved in learning and memory, as well as targeting, labeling and ablating infiltrative high-grade neoplastic, cancer cells. It can also be used, for example, to treat heart afflictions such as acute myocardial ischemia or ventricular arrhythmias.

The normal electrical conduction of the heart allows for electrical propagation to be transmitted from the Sinus Node through both atria and forward to the atrioventricular node (AV). The AV node is part of an electrical control system of the heart that co-ordinates heart rate. It electrically connects atrial and ventricular chambers. Briefly, a heart beat is normally initiated at the level of the sinus node i.e. the electric impulse-generating (pacemaker) tissue located in the right atrium of the heart, and thus the generator of normal sinus rhythm. Normal sinus rhythm is the rhythm of a healthy normal heart, where the sinus node triggers the cardiac activation. When the heart's sinus node is defective, the heart's rhythms become abnormal—either too fast, too slow, or a combination. Abnormal heart's rhythms might result in a decreased transport of oxygen to the cardiac muscle, causing lack of oxygen in the heart muscle. This lack of oxygen in the heart muscle is called a myocardial ischemia. If the oxygen transport is terminated in a certain area, for example due to ischemia, the heart muscle dies in that region. This is called an infarction.

Ventricular arrhythmias is also caused by an abnormal electrical conduction of the heart. Ventricular arrhythmias is defined as abnormal rapid heart rhythms (arrhythmias) that originate in the lower chambers of the heart (the ventricles). Ventricular arrhythmias include ventricular tachycardia and ventricular fibrillation. Both are life threatening arrhythmias. In ventricular arrhythmias, ventricular activation does not originate from the atrioventricular node and/or does not proceed in the ventricles in a normal way.

Both the sinus node and AV node stimulate the cardiac muscle. It is therefore essential to control electric conduction in heart patients such as, for example, in patients who suffer from acute myocardial ischemia or ventricular arrhythmias.

Implantable cardiac pacers and defibrillators are well-established devices that can revert potentially fatal arrhythmias back to a normal sinus rhythm by electrical stimulation of heart tissue. For example, an artificial pacemaker is a medical device which uses electrical impulses, delivered by electrodes contacting the heart muscles, to regulate the beating of the heart. Implantable artificial pacemakers are nowadays currently used in heart patients such as, for example, in patients who suffer from acute myocardial ischemia or ventricular arrhythmias. However, these artificial pacemakers are often associated with an increased risk for cardiac complications because an artificial pacemaker is an implanted bio-mechanical device that requires routine inspection and maintenance.

To optimize stimulation of cardiac tissue, nanodevices can be utilized to target specific cardiac cells. Nanosensors are emerging that can detect hydrogen ions resulting from cardiac ischemic changes. See Ramachandran et al, *Design and fabrication of nanowire electrodes on a flexible substrate for detection of myocardial ischemia*, Proceedings of SPIE Conferences on Nanosensors, Biosensors, and Info-Tech Sensors and Systems; The International Society for Optical Engineering (2009). However, nanosensor-triggered electrical energy-releasing devices do not currently exist that can detect anaerobic metabolism due to a lack of oxygen to trigger release of electrical energy used to defibrillate heart muscle syncytium and/or pacer cells.

Therefore, the energy-releasing nanodevice, disclosed in this application, that can be designed to target specific cells and/or release a tunable level of energy offers a great advantage over the current state-of-the-art implantable devices. Moreover, a plurality of such energy-releasing nanodevices can be delivered at close proximity of the target cells rapidly through minimally invasive methods.

Carbon nanotubes (CNT) were discovered in the early 1990s as a product of arc-evaporation synthesis of fullerenes. See Iijima, *Helical microtubules of graphitic carbon*, Nature 354:56-58 (1991). The name "Carbon nanotubes" is derived from their size, since the diameter of a nanotube is on the order of a few nanometers (approximately 1/50,000th of the width of a human hair).

Carbon nanotubes have unique chemical and physical properties including ultra light weight, high mechanical strength, high electrical conductivity, and high thermal conductivity. See Sinha and Yeow, *Carbon nanotubes for biomedical applications*, IEEE Transactions on NanoBioscience, 30 4:180-195 (2005). These characteristics make CNT a novel nanomaterial for various biomedical applications. See Ji et al, *Carbon nanotubes in cancer diagnosis and therapy*. Biochimica et Biophysica Acta—Reviews on Cancer, 1806(1):29-35 (2010). Recently, research has focused on investigation of targeted delivery of functionalized carbon nanotubes to specific sites of interest. CNT can behave either as a metal or a semiconductor depending on their chiral vector. See Dresselhaus et al., *Carbon Nanotubes: Synthesis, Properties and Applications*, Springer, Berlin (2001). However, many of these properties can be addressed once the CNT are conjugated with different molecules.

CNT are also appropriate nanomaterials based on their unique electrical properties making them a good candidate for overcoming the limitations of convection enhanced delivery (CED) systems. Although CED systems have promising advantages due to the increased volume of drug distribution in the brain, the high pressures required for CED have a high risk of damaging the tissue. Moreover, these high pressures may result in backflows along the catheter causing poor drug distribution. See Sampson et al., *Poor drug distribution as a possible explanation for the results of the PRECISE trial*, Journal of Neurosurgery. 113(2):301-309 (2010).

One category of nanotube is single-walled nanotubes (SWNT). SWNT can exhibit electric properties such as high electrical conductivity that are electrically useful. SWNT are one likely candidate for miniaturizing electronics beyond the micro electromechanical scale currently used in electronics. SWNT can be integrated into complex assemblies through chemical functionalization which utilizes chemical covalent bonding between SWNT and a molecular conjugate. See Ramanathan et al., *Amino-Functionalized Carbon Nanotubes for Binding to Polymers and Biological Systems*. Chemistry of Materials, 17:1290-1295 (2005). An extensive ultrasonic treatment of SWNT allows for an oxidation process that leads to the opening of the tube caps and the formation of holes in the sidewalls introducing oxygen containing groups. This process uses the concept of the Stone-Wales defect that creates these functional groups on 2-3% of the sidewall area of carbon nanotubes. These groups can be chemically modified to create carbon nanotube composites. See Balasubramanian and Burghard, *Chemically Functionalized Carbon Nanotubes*. Small, 1:180-192 (2005). Due to the CNT size and structure they cannot be easily visualized using conventional optical and confocal microscopes. Chemical functionalization with fluorescein labels is one example of a technique for visualizing CNT, and linking associated therapeutic molecules to CNT. In effect, a type of nanocarrier drug delivery or diagnostic system can be developed.

In the prior art, investigational nanotechnology approaches are at a stage that offers a proof of principle demonstrating amelioration of cancer treatment by two emerging strategies. Namely, 1) targeted drug delivery using drugs attached to nanoparticles (See Murad et al, *Real-time, image-guided, convection-enhanced delivery of interleukin 13 bound to pseudomonas exotoxin*, Clin Cancer Res. 12(10):3145-3151 (2006); Liu et al, *Drug delivery with carbon nanotubes for in vivo cancer treatment*. Cancer Res 15; 68(16):6652-6660 (2008)), and 2) targeted release of thermal energy using nanoparticles capable of emitting destructive thermal energy following absorption of external laser or electromagnetic wavelength energies. See Park et al, *Cooperative nanomaterial system to sensitize, target, and treat tumors*. Proc Natl Acad Sci USA 107(3):981-986 (2010); Kam et al, *Carbon nanotubes as multifunctional biological transporters and near-infrared agents for selective cancer cell destruction*. Proc Natl Acad Sci USA. 102(33):11600-11605 (2005); Ganon et al, *Carbon nanotube-enhanced thermal destruction of cancer cells in a noninvasive radiofrequency field*. Cancer. 110(12): 2654-65 (2007).

One significant way to enhance the therapeutic index of anticancer drugs is to specifically deliver these agents directly to tumor cells while being carried by a nanosized carrier. This approach can keep the anticancer drugs away from healthy cells that would otherwise be damaged by the toxic effects of these drugs. See Sapra and Allen, *Ligand-targeted Liposomal Anticancer Drugs*, Progress in Lipid Research 42(5):439-462 (2003). Such target-oriented delivery systems include the delivery of microspheres, nanoparticles and liposomes. See Okada et al, *Gene therapy for brain tumors: cytokine gene therapy using DNA/liposome (series 3)*, No Shinkei Geka 22:999-1004 (1994); Kakinuma et al, *Targeting chemotherapy for malignant brain tumor using thermosensitive liposome and localized hyperthermia*, J Neurosurg 84:180-184 (1996).

Alternatively, instead of delivering anticancer drugs with nanoparticles, other nanoparticles are currently being tested in laboratory conditions to focus energy absorbed from external lasers to ablate tumor cells throughout the body. See Von Maltzahn et al, *Computationally guided photothermal tumor therapy using long-circulating gold nanorod antennas*, Cancer Res 69:3892-3900 (2009).

A fundamental element required for the successful deployment of strategies aimed at targeting particular cells is the ability to identify surface molecules expressed by, for example, tumor cells and absent in surrounding healthy cells. Therefore, neoplasm avid functional biomolecules such as monoclonal antibodies and proteins conjugated to nanoparticles is essential to a tumor cell targeting system. See Huwyler et al, *By-passing of P-glycoprotein using immunolipo-somes*. J Drug Target. 10(1):73-9 (2002).

The expression of the interleukin-13 (IL-13) receptor is one of several targets over-expressed in 60-80% of high-grade astrocytoma cells i.e. cancer cells also known as Gliobalstoma multiforme (GBM). See Kioi et al, *Convection-enhanced delivery of interleukin-13 receptor-directed cytotoxin for malignant glioma therapy*. Technol Cancer Res Treat. 5(3):239-50 (2006). Human IL-13 is a cytokine protein secreted by activated T cells that elicits both pro-inflammatory and anti-inflammatory immune responses. See McKenzie et al, *Interleukin 13, a T-cell-derived cytokine that regulates human monocyte and B-cell function*. Proc Natl Acad Sci USA. 90(8):3735-9 (1993); Minty et al, *Interleukin-13 is a new human lymphokine regulating inflammatory and immune responses*. Nature. 362(6417):248-50 (1993). IL-13 has two receptor subtypes: IL-13/4R and IL-13R-alpha2. The former receptor is present in normal cells with high affinity binding shared with IL-4. The latter receptor, IL-13R-alpha2, does not bind IL-4. See Caput et al, *Cloning and characterization of a specific interleukin (IL)-13 binding protein structurally related to the IL-5 receptor alpha chain*. J Biol Chem. 271(28):16921-6 (1996). IL-13R-alpha2 is associated with high-grade astrocytomas and is not significantly expressed in normal tissue, with the exception of the testes. See Caput et al, 1996; Debinski et al, *Molecular expression analysis of restrictive receptor for interleukin 13, a brain tumor-associated cancer/testis antigen*. Mol Med. 6(5):440-9 (2000). Pilocytic astrocytomas, the most common astrocytic tumors in children, also over express the IL-13R-alpha2 receptor. See Kawakami et al, *Analysis of interleukin-13 receptor alpha2 expression in human pediatric brain tumors*. Cancer. 101(5): 1036-42 (2004). In effect, the IL-13R-alpha2 receptor exists as an excellent potential target for delivering cytotoxic molecules to a variety of devastating brain tumors.

A number of attempts to use the IL-13R-alpha2 receptor of GBM as a target for brain cancer therapy have been reported both in vitro and in vivo. Some of the successful modalities attempted include, IL-13-based cytotoxins (See Nash et al, *Molecular targeting of malignant gliomas with novel multiply-mutated interleukin 13-based cytotoxins*. Crit Rev Oncol Hematol. 39(1-2):87-98 (2001); Husain & Puri, *Interleukin-13 receptor-directed cytotoxin for malignant glioma therapy: from bench to bedside*. J Neurooncol. 65(1):37-48 (2003); Kioi et al, (2006); Murad et al, (2006)), IL-13R-alpha2-targeted viruses (See Zhou et al, *Engineered herpes simplex virus 1 is dependent on IL-13R-alpha2 receptor for cell entry and independent of glycoprotein D receptor interaction*. Proc Natl Acad Sci USA. 99(23):15124-9 (2002)), and IL-13R-alpha2 immunotherapy (See Mintz et al, *Molecular targeting with recombinant cytotoxins of interleukin-13 receptor alpha2-expressing glioma*. J Neurooncol. 64(1-2):117-23 (2003); Kawakami et al, *Intratumor administration of interleukin-13 receptor-targeted cytotoxin induces apoptotic cell death in human malignant glioma tumor xenogratls*. Mol Cancer Ther. 1(12):999-1007 (2002)).

As a nanocarrier, CNT have been utilized as excellent candidates for attaching drug molecules, and imaging markers from radiotracers (See Singh et al, *Tissue biodistribution and blood clearance rates of intravenously administered carbon nanotube radiotracers*. Proc Natl Acad Sci USA. 103(9): 3357-62 (2006)) to colorimetric labels (See Lee et al, *Carbon nanotube-based labels for highly sensitive colorimetric and aggregation-based visual detection of nucleic acids*. Nanotechnol. 18(45) 455102.1-455102.9 (2007)). Although metal contaminants used to catalyze the synthesis of CNT can potentially contribute to toxicity, biocompatibility can be achieved with new CNT purification techniques. See Lu et al, *Advances in bioapplications of carbon nanotubes*. Adv Materials. 21:139-152 (2009); Liu et al, *Drug delivery with carbon nanotubes for in vivo cancer treatment*. Cancer Res. 68(16): 6652-60 (2008); Schipper et al, *A pilot toxicology study of single-walled carbon nanotubes in a small sample of mice*. Nat Nanotechnol. 3(4):216-21 (2008); Yang et al, *Long-term accumulation and low toxicity of single-walled carbon nanotubes in intravenously exposed mice*. Toxicol Lett. 181(3): 182-9 (2008). Moreover, neural cells have demonstrated a preference for growing on CNT scaffolding. See Lee & Parpura, *Wiring neurons with carbon nanotubes*. Front Neuroengineering. 29; 2:8 (2009). CNT are promising nanoscaffolds for transporting biological ligands for diagnostic and therapeutic purposes including crossing cell membranes, particularly for proteins less than 80 kDa. See Panarotto et al, *Translocation of bioactive peptides across cell membranes by carbon nanotubes*. Chem Commun (Camb). (1):16-7 (2004). Once a protein ligand is bound to CNT, it has been shown to remain bound under ambient conditions. See Gruner, *Carbon nanotube transistors for biosensing applications*. Anal Bioanal Chem. 384(2):322-35 (2006).

The conducting ability of CNT makes these carbon-rich nanostructures impressive electromagnetic energy transducers. See Khatpal et al, *Polyfunctionalized single-walled carbon nanotubes as a versatile platform for cancer detection and targeted dual therapy*. Intel STS Abstract (2009). The carbon atoms comprising the building blocks of CNT demonstrate a defined periodicity throughout the nanostructure. This property gives CNT the ability to efficiently transfer electrons. Therapeutically, these electronic properties of CNT along with the significant surface area of CNT can be harnessed. For example, the CNT backbone of such novel nanostructures potentially can be transported through a medium using an electromagnetic field. In addition, the semiconducting properties of CNT can potentially deliver focused energy to ablate neoplastic cells by converting radiofrequencies into heat. See Gannon et al, *Carbon nanotube-enhanced thermal destruction of cancer cells in a noninvasive radiofrequency field* Cancer. 110(12):2654-65 (2007).

The technologies described in the prior-art differ from the invention disclosed in this application. The invention disclosed in this invention relies on nanotechnology that can be applied to treat, for example, brain cancers, cardiovascular diseases and brain afflictions such as epilepsy.

This application describes a novel nanoparticle. It also describes the method of using it to therapeutically treat cells inside patient tissue by delivering electrical energy to those cells. The nanoparticle possesses a molecular detection system and a nanocapacitor. The nanoparticle discharges electrical energy to cells even when those cells are found deeply embedded in a patient's tissue. Self-contained nanosensors that are integrated with nanocapacitor charging capability to stimulate the microenvironment in response to local changes do not exist in the prior-art. This disclosure describes a novel nanoparticle of up to 500 nanometers in diameter since it has been shown that a nanoparticle of up to 500 nanometers in diameter is capable of crossing the blood-brain barrier in certain disease states such as epilepsy and brain cancers.

The present disclosure also relates to nanoparticles that can be made to discharge different amounts of energy. These novel nanoparticles can be concurrently introduced into one or more epileptic circuits in the brain to detect changes during seizure activity (e.g., nanomolar increases in the transmitter glutamate). A detection threshold can be used to discharge the nanocapacitor of these novel nanoparticles to deliver direct stimulation therapy to potentially stabilize the epileptic circuit. By releasing specific amounts of energy, the nanoparticles of the current disclosure can also damage or destroy disease-inducing cells, stabilize the activity of neurons or other cells such as cardiac cells. The present disclosure also relates to nanoparticles that contain a nanocapacitor that can be recharged in energy once the nanoparticles have been discharged.

BENEFITS OF THE INVENTION

It is a first benefit of the present invention to provide an energy-releasing carbon nanotube transponder to deliver at least one electric charge to a tissue.

It is a further benefit of the instant invention to provide a method for the energy-releasing carbon nanotube transponder to release a biologically nondestructive electric charge.

It is another benefit of the invention to provide a method for the energy-releasing carbon nanotube transponder to release a biologically destructive electric charge.

It is an additional benefit of the invention to provide a method to treat cancer, for example brain cancer.

It is still an additional benefit of the invention to provide a method to stabilize brain electrical circuits, for example in patients who suffer from seizures or epilepsy.

Another additional benefit of the invention is to provide a method to treat cardiac disease, for example in patients who suffer from acute myocardial ischemia or ventricular arrhythmias.

These and other benefits of the invention will more readily become apparent from the description and examples which follow.

BRIEF DESCRIPTION OF THE DRAWINGS

FIG. 1 is a diagram of an energy-releasing carbon nanotube transponder 10.

Optionally, a biomolecule ligand 14 is covalently attached to an end of at least one carbon nanotube 12 to form a nanosensor 16 i.e. sensing element of the present disclosure. A nanocapacitor 18 is connected to the opposite end of at least one of the carbon nanotube 12. The association of the optional biomolecule ligand 14, at least one carbon nanotube 12 and the nanocapacitor 18 forms the energy-releasing carbon nanotube transponder 10. Optionally, the outer surface of the energy-releasing carbon nanotube transponder 10 can be coated with at least one biocompatible molecule to form a biocompatible coating 20, for example to improve cellular binding or body tolerance towards the energy-releasing carbon nanotube transponder 10. Optionally, at least one molecular label 22 such as a radiolabel is covalently attached to an end of at least one carbon nanotube 12 to allow for in vivo tracking of the energy-releasing carbon nanotube transponder 10. Optionally, a coiled nanowire located inside (24a) the nanocapacitor 18, or alternatively by design, outside (24b) the nanocapacitor 18, allows for the energy-releasing carbon nanotube transponder 10 to be recharged in energy once it has been discharged.

SUMMARY OF THE INVENTION

According to an embodiment of the present disclosure, an energy-releasing carbon nanotube transponder is provided. A transponder is normally defined as an automatic device that transmits a predetermined signal in response to a predefined received signal. However, the term transponder is used in an unconventional way in this application. In the present disclosure, at the cellular level, the energy-releasing carbon nanotube transponder can transmit an electrical discharge in response to the binding of a specific biomolecule ligand to its cellular receptor and/or the detection of a specific electrical field condition and/or the detection of a predetermined concentration of specific chemicals in the environment of the energy-releasing carbon nanotube transponder.

The energy-releasing carbon nanotube transponder includes at least one carbon nanotube connected to a nanocapacitor. Optionally, a nanosensor is formed by at least one biomolecule ligand covalently attached to an end of at least one carbon nanotube. The nanocapacitor is connected to the opposite end of at least one of the carbon nanotube.

According to an embodiment of the present disclosure, the association of the nanocapacitor to the nanosensor forms the energy-releasing carbon nanotube transponder. The energy-releasing carbon nanotube transponder is optionally coated with at least one biocompatible molecule to form a biocompatible coating. The energy-releasing carbon nanotube transponder is optionally labeled with at least one molecular label.

According to an embodiment of the present disclosure, the energy-releasing carbon nanotube transponder releases a biologically non-destructive electric charge to target cells.

According to an embodiment of the present disclosure, the energy-releasing carbon nanotube transponder releases a biologically destructive electric charge to target cells.

According to an embodiment of the present disclosure, a method for damaging disease-promoting cells is provided. The method includes the step of positioning the energy-releasing carbon nanotube transponder disclosed in this application in the biological tissue to be treated.

According to an embodiment of the present disclosure, a method for treating cancer is provided. The method includes the step of positioning the energy-releasing carbon nanotube transponder disclosed in this application in the cancer tissue to be treated. The method includes the step of delivering a biologically destructive charge in the cancer tissue in order to treat cancer cells.

According to an embodiment of the present disclosure, a method for modifying the electric field within cellular tissues is provided. The method includes the step of positioning the energy-releasing carbon nanotube transponder disclosed in this application in the biological tissue to be treated.

According to an embodiment of the present disclosure, a method for treating epilepsy is provided. The method includes the step of positioning the energy-releasing carbon nanotube transponder disclosed in this application in the brain tissue to be treated. The method includes the step of delivering a biologically non-destructive charge in the brain tissue in order to stabilize electrical circuits in the brains of patients with epilepsy.

According to an embodiment of the present disclosure, a method for treating cardiac disease is provided. The method includes the step of positioning the energy-releasing carbon nanotube transponder disclosed in this application in the tissue that affects cardiac functions. The method includes the step of delivering a biologically non-destructive charge in the heart-related tissue in order to treat cardiac disease (e.g. acute myocardial ischemia and ventricular arrhythmias).

DESCRIPTION OF THE PREFERRED EMBODIMENTS

While the present disclosure may be embodied in many different forms, and may be used to affect various cellular tissues, a number of illustrative embodiments are described herein with the understanding that the present disclosure is to be considered as providing examples of the principles of the invention and such examples are not intended to limit the invention to preferred embodiments described or illustrated.

Referring to the FIGURE, the energy-releasing carbon nanotube transponder 10 integrates at least one carbon nanotube 12 attached to a nanocapacitor 18. Optionally, the energy-releasing carbon nanotube transponder 10 also integrates at least one carbon nanotube 12 attached to a biomolecule ligand 14 in order to form a nanosensor 16 subassembly. Optionally, the energy-releasing carbon nanotube transponder 10 also integrates at least one carbon nanotube 12 attached to a molecular label 22. Optionally, a coiled nanowire located inside (24a) the nanocapacitor 18, or alternatively by design, outside (24b) the nanocapacitor 18, allows for the energy-releasing carbon nanotube transponder 10 to be recharged in energy once it has been discharged.

Carbon nanotubes 12 can be synthesized through methods well-known in the art. These methods include: electric arc discharge, laser ablation, and catalytic chemical vapor deposition (CCVD). See Iijima, *Helical microtubules of graphitic carbon*, Nature 354:56-58 (1991); Thess et al, *Clystalline ropes of metallic carbon nanotube*, Science 273: 483-487 (1996); Yudasaka et al, *Singlewalled nanotube formation by laser ablation using double-targets of carbon and metal*, Chem Phys Lett 278:102-106 (1997); Baddour and Briens, *Carbon nanotube synthesis: a review*, Int. J Chem Reactor Eng 3:R (2005).

An operative embodiment can make use of a plurality of single wall carbon nanotubes 12 (SWCNT) characterized by electric conductivity and biocompatibility. SWCNT are like a sheet of carbon atoms rolled into a cylinder that is about 3.5 nanometers in diameter (about 1/50,000 the diameter of a human hair), however, the present disclosure also encompasses the utilization of other carbon nanotubes. SWCNT possess characteristics of a conductive metal. It has been shown that the interior of the SWCNT cylinder can guide electrons down its length. This innate conductivity can be altered along the nanotube by attaching, for. example, biomolecules such as biomolecule ligands. See Chen et al, *An investigation of the mechanisms of electronic sensing of protein adsorption on carbon nanotube devices*. J Am Chem Soc. 126(5):1563-8 (2004); Ishikawa et al, *Rapid and label-free cell detection by meta/cluster-decorated carbon nanotube biosensors*. Biosensors Bioelectronics 24: 2967-2972 (2007); Chen et al., *Functionalized single-walled carbon nanotubes as rationally designed vehicles for tumor-targeted drug delivery*, J. Am. Chem. Soc. 130:16778-16785 (2008); Ishikawa et al, *Label-free, electrical detection of the SARS virus N-protein with nanowire biosensors utilizing antibody mimics as capture probes*. ACS Nano. 3(5):1219-24 (2009).

One optional way to alter the electrical conductivity of a carbon nanotube 12 is by attaching at least one biomolecule to it. Such a biomolecule can be covalently attached to a carbon nanotube by the sharing of pairs of electrons between atoms. These biomolecules can be ligands for receptors i.e. biomolecule ligand 14. The binding of ligands to receptors occurs by intermolecular forces, such as ionic bonds, hydrogen bonds and Vander Waals forces.

The response of a nanosensor 16 involves three characteristics; 1) the electrostatic interaction between the net charge of a biomolecule, a carbon nanotube and counter ions in buffer; 2) movement or transport of the biomolecule to a receptor or marker and 3) alteration of the conductance of the carbon nanotube 12. For example, a nanosensor 16 formed by the attachment of a biomolecule ligand 14 to a carbon nanotube 12 can be introduced into one or more epileptic circuits to detect changes during seizure activity (e.g., femtomolar increases in the neurotransmitter glutamate correlates to an increased conductivity of the carbon nanotube 12 of the nanosensor 16. A detection threshold of the energy-releasing carbon nanotube transponder 10 can be used to discharge a nanocapacitor 18 to deliver direct stimulation therapy to potentially stabilize the epileptic circuit.

A capacitor functions much like a battery but charges and discharges much more efficiently. A nanocapacitor 18 is a nanostructure large enough to connect to at least one carbon nanotube 12. The nanocapacitor 18 has a capacity for storing an electric charge appropriate to its application. The method of charging the nanocapacitor 18 is according to the requirements of the particular nanocapacitor 18. An example of a suitable nanocapacitor can be provided by a nanotechnology company such as SolRayo, Inc, Madison, Wis. Optionally, a coiled nanowire located inside (24a) the nanocapacitor 18, or alternatively by design, outside (24b) the nanocapacitor 18, allows for the energy-releasing carbon nanotube transponder 10 to be recharged in energy once it has been discharged.

In the first exemplary embodiment, the nanocapacitor 18 and the energy-releasing carbon nanotube transponder 10 release biologically destructive electric charge densities in the range of between about 21 and about 30 microCoulombs/ cm² and preferably about 23 microCoulombs/cm². In the second exemplary embodiment, the nanocapacitor 18 and the energy-releasing carbon nanotube transponder 10 release biologically non-destructive electric charge densities in the range of between about 4 and about 20 microCoulombs/cm².

Noncovalent functionalization of carbon nanotube 12 can be performed to preserve the bioactivity of the biomolecule ligand 14. See Panchapakesan et al, *Single-wall carbon nanotubes with adsorbed antibodies detect live breast cancer cells*, Nano Biotech 1:353-360 (2005). Detection of a bound ligand and biomolecules has been performed by monitoring the electrical current through the carbon nanotube 12 under a 5 mV bias during ligand and biomolecule. Charge transfer has been shown to occur between carbon nanotube 12 bound antibodies and certain cancer cells to which the antibodies can bind. Binding to an antigen-specific antibody can produce a several-fold increase in electrical conductance of the carbon nanotube 12 compared to binding using nonspecific antibodies. Ibid.

Antibodies or proteins associated with particular afflictions are first identified using common biomolecular methodologies. For example, a glutamate detecting protein construct ligand has been identified and used for detection of nanomolar changes of the transmitter glutamate at the surface of living cells. See Okumoto et al, *Detection of glutamate release from neurons by genetically encoded surface-displayed FRET nanosensors*, PNAS 102:8740-8745 (2005). Another example is carbon nanotube 12 binding to high grade brain glioma cells expressing human interleukin-13R-alpha2 (IL-13Ra2) receptors. See Minty et al, *Interleukin-13 is a new human lymphokine regulating inflammatory and immune responses*, Nature 362:248-250 (1993); McKenzie et al, *Interleukin 13, a T-cell-derived cytokine that regulates human monocyte and B-cell function*, Proc Natl Acad Sci USA 90:3735-3739 (1993). The IL-13R-alpha2 receptor is a specific cell membrane biomarker for cancer cells. IL-13 is an example of biomolecule ligand for the IL-13R-alpha2 receptor. Ligand binding to a carbon nanotube can be optimized to generate large quantities of nanoparticles suitable for patient treatment. The services of a company such as Phosphorex, Inc, Fall River, Mass., can be used for that purpose and, for example, to optimize the binding of the biomolecule ligand IL-13 onto carbon nanotubes. The biomolecule ligand 14 specific to the receptors/markers are then produced and covalently linked to at least one carbon nanotube 12 to form the nanosensor 16 element of the present disclosure.

Alternatively, the nanosensor 16 element of the invention can be calibrated in order to allow for the release of electrical energy from the nanocapacitor 18 at a pre-determined modification in the conductivity of the carbon nanotube 12. More specifically, the presence of the energy-releasing carbon nanotube transponder 10 in a pre-determined electrical field suffices to trigger the release of the stored electrical energy from the nanocapacitor 18 even in absence of binding between a biomolecule ligand 14 and its receptor.

Optionally, a biocompatible coating 20 surrounds the energy-releasing carbon nanotube transponder 10, for example, to improve bio tolerance and/or adherence of the energy-releasing carbon nanotube transponder 10 onto target cells. For example, the nanotransponder presently disclosed can be coated with an amphilic copolymer, such as PEG molecules, that can enhance biocompatibility of the nanodevice. Similar polymers have been used in drug delivery. See Allen et al, *Nano-engineering block copolymer aggregates for drug delivery*, Colloids Surf B: Biointerfaces 16:3-27 (1999). The charged transponder 10 can be carefully inserted in a cellular tissue with a probe, needle or catheter for example. See Rossi, *Optimizing termination of the ictal onset: On-demand pulsatile intracerebral delivery of RWJ-333369 with responsive neurostimulation*, Johnson & Johnson Grant PAR-2007-0001255 (2007). Suitable neural probes can be purchased from companies such as NeuroNexus Technologies, Inc., Ann Arbor, Mich. NeuroNexus fluidic microelectrode probes can allow for a very precise positioning of nanoparticles in the brain. Neural probes can also be used to measure alterations in local electric fields generated by neurons. For therapeutic applications, a plurality of energy-releasing carbon nanotube transponders 10 can be implanted within a tissue to be treated. The required number of energy-releasing carbon nanotube transponder is typically greater than 1000 but can also be smaller as required by treatment.

Alteration in conductivity can be measured across the carbon nanotube 12 using a well-developed cantilever technique to hold the carbon nanotube 12 in place. In practice, depending on the targeted cells, Interleukin-13 can be switched out for any biomolecule ligand 14 of interest to a bioreceptor on or inside a neural cell for example.

Such alteration in conductivity can be precisely measured using a semiconductor parameter analyzer e.g. HP4516, capable of measuring femtoAmps (fA) of electrical current with high accuracy. See Panchapakesan et al, (2005). Accordingly, a method of selecting a ligand from possible ligands to bind to one type of target cells can be selected from known target cell receptor types. One nanocapacitor 18 can store a mean charge density from about $1.2 \times 10^{-5}$ to about $2.4 \times 10^{-5}$ Coulombs/cm². This storage capacity allows for a plurality of energy-releasing carbon nanotube transponders to deliver an electrical charge in the range from about 4 to about 30 microCoulombs/cm².

The amount of electric energy to be administered differs according to various parameters such as for example, the tissue, the localization of the target and the purpose of the treatment. Methods to predict the propagation of electric fields within tissues have been published. They can be utilized to optimize placement of energy-releasing nanotransponders and to determine the optimum amount of electric energy that need to be released. For example, Rossi et at (2010), provide a method to predict propagation pattern of electrical current in brain tissue, including epileptic tissue during neurostimulation therapy. See Rossi et al, *Predicting white matter targets for direct neurostimulation therapy*. Epilepsy Res. 91(2-3): 176-186 (2010). This method predicts the optimum brain location where an electric discharge can be initiated to treat brain afflictions such as for example epilepsy. After electric stimulation of brain tissue, this method allows for the validation of the choice of the location where electric stimuli were previously initiated. Rossi et at (2010) allowed for the determination of the optimum electric charge to be delivered in a human patient who suffered from epileptic seizures. This method allowed for the delivery in a human patient of a biologically non-destructive charge of 9.1 microCoulombs/cm² to abort seizures without injuring brain cells.

The outer surface of the energy-releasing carbon nanotube transponder 10 can be coated with at least one biocompatible molecule 20, for example to improve cellular binding or body tolerance towards the energy-releasing carbon nanotube transponder 10.

Optionally, a molecular label such as a radiolabel 22 is covalently attached to at least one carbon nanotube 12 to allow for in vivo tracking of the energy-releasing carbon nanotube transponder 10. Such molecular label is also useful to insure proper positioning of the energy-releasing carbon nanotube transponder 10. Carbon nanotubes have been utilized for attaching molecular labels such as imaging markers made of radiotracers (See Singh et al, (2006)) and colorimetric labels (See. Lee et al, (2007)). Examples of radiotracers include technetium (99mTc) (See Wu et al, *Covalently combining carbon nanotubes with anticancer agent: preparation and antitumor activity*. ACS Nano. 3(9):2740-50 (2009)) or indium-111 (See. Singh et al, (2006)). Depending on treatment or on the length of time when tracking of the optional molecular label 22 is desired it is possible to use for example indium-111 that possesses a half-life of 67 hours over for example Technetium that possesses a half-life of only 6 hours. In any case, published protocols can easily be adapted to particular needs. For example, Singh et al, (2006) and Wu et al, (2009), provide methods for coupling indium and technetium, respectively, to a carbon nanotube 12.

Optionally, the biomolecule ligand 14-cellular receptor binding event can be detected by a passive Radio Frequency Identification Device (RFID) to trigger a signal to be transmitted to an external receiver. The utilization of a RFID allows for the transmission of data identifying changes in the surrounding micro-environment of the energy-releasing carbon nanotube transponder 10.

In an exemplary embodiment, the nanocapacitor 18 is initially triggered automatically by changes in the microenvironment of the energy-releasing carbon nanotube transponder 10, as known in the art. These changes can be defined as for example, the binding of the biomolecule ligand 14 to a cellular receptor (e.g. the biomolecule ligand IL-13 binding to the cellular receptor IL-13R-alpha2), or a change in ions concentration (e.g. changes in hydrogen ions concentration), or a change in a chemical concentration (e.g. changes in glutamate concentration) or changes in an electric field surrounding the energy-releasing nanoscale transponder 10 (e.g. changes due to modification of the electric field of a brain tissue or a heart tissue). Such changes in the microenvironment of the energy-releasing nanoscale transponder 10 can cause an increase in conductance of at least one carbon nanotube 12 of the energy-releasing nanoscale transponder 10 by a factor of at least 2 to 10 (See Panchapakesan et al, (2005)). Such changes in impedance or conductivity of at least one carbon nanotube 12, function as a nanoswitch that triggers the discharge of the electrical energy stored in the nanocapacitor 18 into the environment of the energy-releasing nanoscale transponder 10.

Several systems and methods have been used for transcutaneously inductively recharging an implantable medical device, as known in the art. Optionally, the electric charge of the nanocapacitor 18 can be maintained, or the nanocapacitor 18 can be recharged through an inductance recharging unit. Inductive charging utilizing an external electromagnetic field is used to transfer energy from the charging station that sends energy through inductive coupling to the nanocapacitor 18 of the implanted energy-releasing carbon nanotube 20 transponder 10.

The inductance recharging unit makes use of a first induction coil to create an alternating electromagnetic field from within the charging base station. In an exemplary embodiment, the nanocapacitor 18 is provided by the company Sol-Rayo (Madison, Wis.). However it can be purchased from other manufacturers. In this exemplary embodiment, the nanocapacitor 18 contains a coiled nanowire 24a that constitutes a second induction coil within the energy-releasing carbon nanotube transponder 10. A coiled nanowire 24a located inside the nanocapacitor 18 constitutes a second induction coil within the energy-releasing carbon nanotube transponder 10.

This coiled nanowire 24a takes power from the electromagnetic field and converts it back into electrical current to charge the nanocapacitor 18 located inside the energy-releasing carbon nanotube transponder 10. The two induction coils, i.e. the coiled nanowire 24a of the nanocapacitor 18, and the induction coil of the inductance recharging unit, in proximity combine to form an electrical transformer. In this exemplary embodiment, the coiled nanowire 24a contained in the nanocapacitor 18 allows for the nanocapacitor 18 to be recharged. Optionally, the coiled nanowire 24a can also be used to externally trigger the nanocapacitor 18 to discharge. This optional functionality of the coiled nanowire 24a can be used to, for example, remotely receive an electromagnetic signal to trigger the release of electric energy from a plurality of energy-releasing carbon nanotube transponders 10 in a predetermined sequence, independently of any other signal. Furthermore, the coiled nanowire 24a can optionally be used to exploit the versatility of a population of transponders to replay a sequence of neural code initially captured by the transponders and transmitted to an external receiver using the Radio Frequency Identification Device (RFID) capability of the carbon nanotube transponder 10.

The charging base station has a shape appropriate to the placement of the energy-releasing carbon nanotube transponder 10, for example, when an energy-releasing carbon nanotube transponder 10 is implanted into the brain, an appropriate shape for the charging base station is, for example, a hat, a helmet or a head scarf.

A carbon nanotube 12 is intrinsically either a conducting or semiconducting carbon-based material. Therefore, it carries electrons in the outer valence shell that by definition make it charged. In fact, carbon nanotubes have more robust and stable electrostatic charge than a natural polymer, like chitosan, which is very pH dependent. Therefore an electric or magnetic field induced within the target tissue is one driving force that can guide a carbon nanotube 12 or an energy-releasing carbon nanotube transponder 10 through a tissue to a target location. An example of a suitable tissue is a brain tissue that is part of the CNS tissue. Beyond guiding a nanodevice to the proper location, an electric or magnetic field can also be used to force an energy-releasing carbon nanotube transponder 10 into a dense tissue such as, for example, a tumor mass or a scar in the brain. Accordingly, and depending on the tissue, it is optionally possible to use electrodes to generate an electric field and guide the energy-releasing carbon nanotube transponder 10 towards a target location. This optional guiding technique can be performed to optimize placement of an energy-releasing carbon nanotube transponder 10 within a tissue. An energy-releasing carbon nanotube transponder 10 can be guided by the electric field produced for example by implanted intracranial electrodes. Suitable electrodes are for example multi-contact extracellular stimulating microelectrode probes (NeuroNexus Technologies, Inc., Ann Arbor, Mich.).

Optionally, the outer surface of the energy-releasing nanoscale transponder 10 can be coated with biocompatible molecules to form a biocompatible coating 20, for example to improve cellular binding or body tolerance towards the energy-releasing carbon nanotube transponder 10. Both biodegradable polymers and non-biodegradable polymers can be used to coat the energy-releasing carbon nanotube transponder 10. Carbon nanotubes and carbon-rich nanocapacitors are considered biocompatible. It is the catalyst contaminants used to produce the nanotubes (e.g., iron, nickel, yttrium) that are potentially toxic. Polymers such as polylactic acid (PLA), polyglycolic acid (PGA) and poly lactide co-glycolide (PLGA) have a long standing history of use for medical applications. They meet the biological requirements of safety and are biodegradable to non-toxic metabolites. They are also approved by the FDA for such use. These polymers are only three examples amongst others of suitable biocompatible coating 20 for the energy-releasing carbon nanotube transponder 10. Another non-limiting example of biocompatible coating 20 for the energy-releasing carbon nanotube transponder 10 is the natural polymer chitosan (i.e. a derivative of chitin from crustacean and insect exoskeletons). See Domb et al, *Biodegradable polymers as drug carrier systems*. In: Polymeric Biomaterials, 2nd edition Dumitriu S (Ed). Marcel Dekker, New York pp 91-121 (2002).

The efficacy of treatment with the energy-releasing carbon nanotube transponder 10 is assessed according to methods well known in the art to determine for example the shrinkage of tumors, the destruction of cancer cells, the reduction in the frequency of epileptic episodes, the abortion of seizures, the improvement of heart rhythms or when applicable methods such as tissue sectioning followed by tissue staining (e.g., Giemsa staining) can be used to visualize cell death and tissue damage.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions. The following examples are illustrative of the invention.

Example 1

In the first exemplary embodiment, tumor-specific nanosensors 16 are created to target brain cancer cells named gliobalstoma multiforme (GBM). An exemplary marker is interleukin-13R-alpha2 (IL-13Ra2). The nanosensor 16, i.e. SWCNT-IL-13Ra2, is formed by attaching at least one carbon nanotube 12 using noncovalent functionalization, to the IL-13Ra2 biomolecule ligand (i.e. IL-13) 14. See Teker, *Bioconjugated carbon nanotubes for targeting cancer biomarkers*, Materials Science Engineering 153(1-3):83-87 (2008). The biomolecule ligand 14 specifically binds to the IL-13Ra2 receptors located on the surface of GBM, but not to other receptors. Therefore, the biomolecule ligand 14 located onto the surface of the energy-releasing carbon nanotube transponder 10 allows for its specific binding onto GBM to minimize subsequent damage to healthy non-cancer cells.

When a biomolecule ligand 14 covalently attached to a carbon nanotube 12 binds to its respective receptor, the conductivity of the carbon nanotube 12 has been shown to increase by two-to-ten orders of magnitude. A change in impedance of the functionalized carbon nanotube 12 (i.e. carbon nanotube 12 linked with a biomolecule ligand of interest 14 e.g. IL-13) can change its conductivity to allow discharging of the nanocapacitor 18.

Accordingly, upon the binding of the biomolecule ligand 14 to a receptor, the nanosensor 16 acts as a nanoswitch. The activation of the nanoswitch permits release of the electrical energy stored in the nanocapacitor 18 into the surrounding environment of the energy-releasing carbon nanotube transponder 10, for example, onto the surface of cancer cells that are then damaged or even destroyed.

In the first exemplary embodiment, the method described in the present disclosure comprises:
identifying brain cancer cells responsible for cancer to be treated;
determining a marker corresponding to said brain cancer cells;
providing a biomolecule ligand 14 specific to the marker;
binding the biomolecule ligand 14 to at least one carbon nanotube 12 to form a nanosensor 16;
connecting at least one nanosensor 16 to a nanocapacitor 18 to form an energy-releasing carbon nanotube transponder 10;
optionally, coating the energy-releasing carbon nanotube transponder 10 with a biocompatible coating 20;
optionally, binding a molecular label 22 to the energy-releasing carbon nanotube transponder 10;
providing a plurality of energy-releasing carbon nanotube transponders 10;
determining an optimum electric charge to be provided to each nanocapacitor 18 for the plurality of energy-releasing carbon nanotube transponders 10 to deliver an electric charge to the brain cancer cells in the range of between about 4 and about 30 microCoulombs/$cm^2$;
storing the optimum electric charge into each nanocapacitor 18 of the plurality of energy-releasing carbon nanotube transponders 10;
placing the plurality of the energy-releasing carbon nanotube transponders 10 proximately to the brain cancer cells;
automatically releasing the optimum electric charge from each nanocapacitor 18 proximately to the brain cancer cells in response to the binding of the biomolecule ligand 14 onto its receptor located onto the surface of the brain cancer cells;
optionally, recharging the plurality of nanocapacitors 18 within the energy-releasing carbon nanotube transponders 10 for allowing multiple treatments; and
assessing treatment efficacy with the plurality of energy-releasing carbon nanotube transponders 10.

Example 2

In a second exemplary embodiment, a nanosensor 16 is created to detect dynamic alterations in the concentration of the neurotransmitter glutamate generated by neurons surrounding brain neoplastic cells. Such microperturbations of glutamate concentration representing epileptiform activity are used to trigger the release of electric energy from the energy-releasing carbon nanotube transponder 20 into the direct environment of the cells associated with epileptic episodes.

A nanosensor 16 formed by the attachment of a biomolecule ligand 14 to a carbon nanotube 12 can be introduced into one or more epileptic circuits to detect changes during seizure activity (e.g., femtomolar increases in the neurotransmitter glutamate correlates to an increased conductivity of at least one carbon nanotube 12 of the nanosensor 16). A detection threshold of the energy-releasing carbon nanotube transponder 10 can be used to discharge a nanocapacitor 18 to deliver direct stimulation therapy to potentially stabilize epileptic circuit.

The nanosensor 16 is bound to a nanocapacitor 18 to form the energy-releasing carbon nanotube transponder 10. In the energy-releasing carbon nanotube transponder 10, at least one carbon nanotube 12 forms a nanowire to conduct the electricity from the nanocapacitor 18 to the area surrounding the energy-releasing carbon nanotube transponder 10.

In this second exemplary embodiment, the method described in the present disclosure comprises:

identifying dynamic alterations in the concentration of a chemical, for example the neurotransmitter glutamate, that correlate with an alteration in local electric fields;

alternatively, identifying a dynamic alteration in local electric fields that is caused by an affliction to be treated;

identifying target cells related to the dynamic alteration in local electric fields;

determining a marker corresponding to the target cells;

identifying a biomolecule ligand 14 specific to the marker of the target cells to be treated;

binding the biomolecule ligand 14 to at least one carbon nanotube 12 to form a nanosensor 16;

connecting at least one said nanosensor 16 to a nanocapacitor 18 to form an energy-releasing carbon nanotube transponder 10;

optionally, coating the energy-releasing carbon nanotube transponder 10 with a biocompatible coating 20;

optionally, binding a molecular label 22 to the energy-releasing carbon nanotube transponder 10;

providing a plurality of energy-releasing carbon nanotube transponders 10;

determining an optimum electric charge to be provided to each nanocapacitor 18 for the plurality of energy-releasing carbon nanotube transponders 10 to deliver a biologically non-destructive electric charge to the target cells in the range of between about 4 and about 20 microCoulombs/cm$^2$;

storing the optimum electric charge into each nanocapacitor 18 of the plurality of energy-releasing carbon nanotube transponders 10;

placing the plurality of energy-releasing carbon nanotube transponders proximately to the target cells;

automatically releasing the optimum electric charge from each nanocapacitor proximately to the target cells in response to dynamic alterations in the concentration of, in this exemplary embodiment, the neurotransmitter glutamate;

optionally, recharging the plurality of nanocapacitors 18 within the energy-releasing carbon nanotube transponders 10 for allowing multiple treatments; and assessing treatment efficacy with the plurality of energy-releasing carbon nanotube transponders 10.

Example 3

In a third exemplary embodiment, a carbon nanotube transponder 10 is created to react to dynamic alterations in the concentration of hydrogen ions resulting from cardiac ischemic changes. Acute myocardial ischemia is triggered by insufficient blood flow to the heart. Acute myocardial ischemia, and other heart conditions such as for example ventricular arrhythmias, decrease the level of oxygen and induce anaerobic metabolism within cardiac tissue. Diseases such as, for example, acute myocardial ischemia or ventricular arrhythmias are the direct consequences of a disregulation of the electrical conduction system of the heart.

To optimize stimulation of cardiac tissue, a plurality of energy-releasing carbon nanotube transponders 10 can be utilized to target specific cardiac cells. Microperturbations in hydrogen ions concentration allow for the detection of anaerobic metabolism due to a lack of oxygen within cardiac tissue. The energy-releasing carbon nanotube transponder 10, can be placed at various locations inside an appropriate heart tissue to trigger release of electrical energy used to defibrillate heart muscle syncytium and/or pacer cells in response to microperturbations in hydrogen ion concentrations.

In this third exemplary embodiment, placement of a plurality of energy-electric carbon nanotube transponders 10 within an appropriate tissue of the electrical conduction system of the heart, for example, the atrioventricular node or the sinus node, can trigger the release of electric energy from the energy-electric carbon nanotube transponder 10 to alter the electrical propagation within the heart muscle of heart patients suffering from for example acute myocardial ischemia or ventricular arrhythmias.

A plurality of energy-electric carbon nanotube transponders 10 can be introduced into one or more electrical conduction circuit of the heart to react to changes in hydrogen ions concentration during cardiac ischemic changes (e.g., femtomolar increases in hydrogen ions concentration correlates with an increased conductivity of at least one carbon nanotube 12). A detection threshold of the energy-releasing carbon nanotube transponder 10 can be used to discharge a nanocapacitor 18 to deliver direct stimulation therapy to the electrical conduction circuit of the heart. In the energy-releasing carbon nanotube transponder 10, at least one carbon nanotube 12 forms a nanowire to conduct the electricity from the nanocapacitor 18 to the area surrounding the energy-releasing carbon nanotube transponder 10.

In this third exemplary embodiment, the method described in the present disclosure comprises:

identifying dynamic alterations in concentration of ions, for example hydrogen ions, that correlate with an alteration in the electrical conduction system of the heart;

alternatively, identifying a dynamic alteration in the electrical conduction system of the heart that is caused by an affliction to be treated;

identifying target cells related to the dynamic alteration in the electrical conduction system of the heart;

optionally, identifying a biomolecule ligand 14 specific to the cells of a tissue to be treated;

optionally, binding the biomolecule ligand 14 to at least one carbon nanotube 12;

binding at least one the carbon nanotube 12 to a nanocapacitor 18 to form an energy-releasing carbon nanotube transponder 10;

optionally, coating the energy-releasing carbon nanotube transponder 10 with a biocompatible coating 20;

optionally, binding a molecular label 22 to the energy-releasing carbon nanotube transponder 10;

providing a plurality of energy-releasing carbon nanotube transponders 10;

determining an optimum electric charge to be provided to each nanocapacitor 18 for the plurality of energy-releasing carbon nanotube transponders 10 to deliver a biologically non-destructive electric charge to the target cells in the range of between about 4 and about 20 microCoulombs/cm$^2$;

storing the optimum electric charge into each nanocapacitor 18 of the plurality of energy-releasing carbon nanotube transponders 10;

placing the plurality of energy-releasing carbon nanotube transponders 10 proximately to the target cells;

automatically releasing the optimum electric charge from each nanocapacitor proximately to the target cells in response to dynamic alterations in the concentration of, in this exemplary embodiment, hydrogen ions; or in response to dynamic alterations in the electrical conduction system of the heart that is caused by the affliction to be treated;

optionally, recharging the plurality of nanocapacitors 18 within the energy-releasing carbon nanotube transponders 10 for allowing multiple treatments; and assessing treatment efficacy with the plurality of energy-releasing carbon nanotube transponders 10.

Example 4

In a fourth exemplary embodiment the optional molecular label 22 is technetium (99mTc) that can be used to check for the proper placement of an energy-releasing carbon nanotube transponder 10 or a component of an energy-releasing carbon nanotube transponder 10 (e.g., carbon nanotube 12).

In this exemplary embodiment, the 99mTc-carbon nanotube 12 scaffold is synthesized from amine functionalized water soluble CNT. The covalent attachment of multiple linker amine groups of diethylenetriaminepentaacetic (DTPA) to a carbon nanotubes 12 backbone is utilized as avid coupling sites for the chelator 6-hydrazine nicotinamide (HyNic) bound to 99mTc. DTPA anhydride is highly soluble in water and follows a simple conjugation chemistry to link two amino groups at the carbon nanotubes 12 surface. The 99mTc radioisotope is obtained as technetium pertechnetate ($99mTcO_4^-$) (Covidien Pharmaceuticals, Hazelwood, Mo.) as an aqueous solution and used without further purification. 99mTc decays by isomeric transition with a physical half-life of 6 hours. Therefore, this molecular label 22 can be easily placed onto carbon nanotube 12 of the energy-releasing carbon nanotube transponder 10 prior to use, in vivo. Thanks to its molecular label 22, the precise location of an energy-releasing carbon nanotube transponder 10 can be determined and visualized by using for example a Single photon emission computed tomography (SPECT) scanner (e.g. inSPira® SPECT scanner, NeuroLogica Corporation, Danvers, Mass.).

An exemplary protocol to form the 99mTc-carbon nanotube 12 conjugate is directly derived from the protocol published by Wu et al. (2009). Pure semiconducting SWNT (Nanointegris, Inc, Skokie, Ill.) (5.5 mg, 2.75 µmol) at a length of 200-500 nm is dissolved in 1 ml of anhydrous DMSO and neutralized with diisopropylethylamine (DIEA) (1 µl; 5.9 µmol). DTPA dianhydride (590 µg; 1.65 µmol) is added, and the mixture is stirred for 3 hr at room temperature. The DMSO solution is diluted with deionized water (5 ml) and lyophilized twice in a VACUFUGE® (Eppendorf North America, Hauppauge, N.Y.). The crude DTPA-CNT derivative is re-precipitated from methanol/diethyl ether several times and lyophilized again from water. The number of the free amino groups remaining on the CNT is measured by the quantitative Kaiser test. A ratio of unreacted amines is determined by calculating the ratio between the number of amino groups on this CNT and the amount of DTPA used. As a result, the CNT is functionalized with amine side-groups. The functionalized CNT is obtained in powder form for complexation with technetium (99mTc), itself an example of molecular label 22.

CNT functionalized with amine side-groups is labeled with the molecular label 22 i.e. 99mTc in this example using the HyNic spacer. Succinimidyl 6-hydrozinium nicotinate (SHNH) is used to link HyNic-DTPA-CNT with $99mTcO_4^-$. SHNH is a bifunctional aromatic hydrazine linker that forms a stable bis-aryl hydrazone bond between $99mTcO_4^-$ and the HyNic-DTPA-CNT complex. 5 ml of HyNic-DTPA-CNT is suspended in 1000 µl of SoluLink modification buffer (pH 7.4) (Solulink, Inc., San Diego, Calif.). A stock solution of SHNH is prepared in anhydrous DMSO for immediate use by dissolving 2-4 mg of SHNH in 100 µl DMSO. The requisite volume of SHNH/DMSO is added to the HyNic-DTPA-CNT solution and incubated for 120 minutes. The DMSO buffer is exchanged with 0.1M sodium phosphate, and 0.15M sodium chloride, (pH 6.0) using Zeba Desalt spin columns (Thermo Scientific, Rockford, Ill.). The resulting solution is injected into a vial containing an aqueous solution of $99mTcO_4^-$ (Covidien Pharmaceuticals, Hazelwood, Mo.) to form the molecular label 22-carbon nanotube 12 conjugate.

Example 5

In a fifth exemplary embodiment a molecular ligand 14 is interleukin-13 (IL-13), however, an example of a suitable molecular ligand 14 is not limited to IL-13. In this exemplary embodiment, the IL-13-carbon nanotube 12 scaffold is synthesized from amine functionalized water soluble CNT. The covalent attachment of multiple linker amine groups of diethylenetriaminepentaacetic (DTPA) to a carbon nanotubes 12 backbone is utilized as avid coupling sites for the chelator 6-hydrazine nicotinamide (HyNic) bound to IL-13. DTPA anhydride is highly soluble in water and follows a simple conjugation chemistry to link two amino groups at the carbon nanotubes 12 surface. To bind IL-13 to carbon nanotube 12, lyophilized human recombinant IL-13 (Pro Spec-Tany TechnoGene Ltd, Rehovot, Israel) is acquired as a single non-glycosylated polypeptide containing 112 amino acids with a molecular weight of 12 kDa. This freeze-dried powder is reconstituted in sterile water at 10 ug in 1 ml. This solution is mixed with the a HyNic-DTPA-CNT complex, as prepared in Example 4, for 1 hr at room temperature to form a biomolecule ligand 14-carbon nanotube 12 complex. Optionally, this IL-13 solution is mixed with a molecular label 22-carbon nanotube 12 conjugate such as 99mTc-HyNic-DTPA-CNT complex, as prepared in Example 4, for 1 hr at room temperature to form a molecular label 22-biomolecule ligand 14-carbon nanotube 12 complex. After this simple mixing step, proteins have been shown to self-assemble and adhere to the nanotube sidewalls remaining bound under ambient conditions. See Azamian et al, *Bioelectrochemical single-walled carbon nanotubes*. J Am Chem Soc. 124(43):12664-5 (2002).

Example 6

In a sixth exemplary embodiment, a plurality of energy-releasing carbon nanotube transponder 10 is placed within the white matter of a human brain to propagate a non-destructive electric charge in an epileptic tissue to subsequently abort epileptic seizures. In this exemplary embodiment, an energy-releasing carbon nanotube transponder 10 is labeled with technetium (99mTc), a molecular label 22. Thanks to this molecular label 22, the precise location of an energy-releasing carbon nanotube transponder 10 can be determined and visualized by using for example single photon emission computed tomography (SPECT) scanner (e.g. inSPira® SPECT scanner, NeuroLogica Corporation, Danvers, Mass.). The optimum placement of the energy-releasing carbon nanotube transponder 10 is determined by using a combination of four techniques known in the art. The first technique is subtracted-ictal SPECT co-registered to MRI. The second technique is subtracted post-ictal diffusion tensor imaging (spiDTI) that is used to assess anatomically specific changes in fractional anisotropy (FA) compared to baseline axonal water diffusion during the early post-ictal period of a focal-onset complex partial seizure. The third technique employs finite element method (FEM) modeling to predict the maximal electric field magnitude immediately surrounding a plurality of carbon nanotube transponder 10. The volume of cortical activation (VOCA) is calculated from the greatest magnitude of the electric field immediately surrounding a plurality of carbon nanotube transponder 10. The fourth technique is diffusion tensor tractography. Once the optimum placement is determined, a plurality of energy-releasing carbon nanotube transponder 10 is precisely positioned in the epileptic tissue using NeuroNexus fluidic microelectrode probes from (NeuroNexus Technologies, Inc., Ann Arbor, Mich.). A plurality of energy-releasing carbon nanotube transponders 10 can be electrically charged using an inductance-based charging base station that has an appropriate shape i.e. that shape of a helmet. Once in the brain, the plurality of energy-releasing carbon nanotube transponder 10 can be electrically discharged. In this exemplary embodiment, the plurality of energy-releasing carbon nanotube transponder 10 propagates a non-destructive charge of 9.1 microCoulombs/$cm^2$ in the epileptic tissue of a human patient. Once discharged, the energy-releasing carbon nanotube transponder 10 is recharged by inductance, as known in the art, for performing multiple treatments with electric stimulations of the epileptic tissue to abort epileptic seizures.

Example 7

In a seventh exemplary embodiment, the energy-releasing carbon nanotube transponder 10 is labeled with fluorescein i.e. the optional molecular label 22. This exemplary embodiment allows for in vitro characterization of the electric field that is optionally required to guide the migration of the energy-releasing carbon nanotube transponder 10. Once defined by using this exemplary embodiment, this electric field is recreated in of a human brain tissue using NeuroNexus fluidic microelectrode probes from (NeuroNexus Technologies, Inc., Ann Arbor, Mich.). Since this electric field is biocompatible, it allows for a controlled migration of a plurality of energy-releasing carbon nanotube transponder 10 in vivo, in the brain of an epileptic patient. In this exemplary embodiment a 0.5% agarose gel produces a porosity similar to that of a human brain. To allow for subsequent fluorescence labeling of SWNT, a plurality of carbon nanotubes 12 is first oxidized according to the following method: 5 mg dry semiconducting SWNT 90-95% purity (NanoIntegris, Inc, Skokie, Ill.) are treated with 8M concentrated solution of sulfuric and nitric acid. The SWNT are then sonicated for 5 hours at 60° C. in an ultrasonic bath (Model FS60D, Fisher Scientific, part of Thermo Fisher Scientific, Rockford, Ill.) to introduce carboxylic acid groups on the SWNT surface. Carboxylation allows for covalent bonding of amide linkages that are used to functionalize SWNT. Carboxylated SWNT are centrifuged at 3.5 k rmp for 10 min. The supernatants is collected and added to 150 mL of cold deionized distilled water. The supernatant is then filtered through a 0.22 µm pore size polycarbonate filter paper (i.e. Isopore Membrane, polycarbonate, Hydrophilic, 0.22 µm, Cat. No. GTTP02500, Millipore, Billerica, Mass.). The filtrand is washed with distilled water until no residual acid is present. The filtrand is then dispersed in ethanol. The filtrand is dried in a vacuum oven at (−20 in. Hg) 80° C. overnight. At least one carbon nanotube 12 of an energy-releasing carbon nanotube transponder 10 is labeled with fluorescein according to the following method:

One milligram of the oxidized semiconducting nanotubes 12 is treated with 0.1M 2-(N-morpholino) ethanesulfonic acid (Fisher Scientific) (MES buffer), 10 mM 1-ethyl-3-(3-dimethylaminopropyl) carbodiimide (EDC) (Sigma Aldrich, St Louis, Mo.) and 1M Fluorescein-5-thiosemicarbazide (FITC) (Sigma Aldrich). This mixture is then dispersed by sonication for 5 min and stirred for 3 h and deionized water is subsequently used to dilute this mixture. The diluted mixture is then centrifuged at 7.0 k rmp for 10 min. The supernant with free FITC is removed and the process is repeated until all free FITC is removed.

Each step of the process of chemical functionalization of the SWNT is verified, for example, by Fournier Transform Infrared Spectroscopy (FTIR). In this exemplary embodiment, FTIR is used to verify each step of the SWNT chemical functionalization process according to the following analytical procedure: A plurality of oxidized carbon nanotubes 12 is dried in a vacuum oven (−20 in. Hg) at 80° C. overnight prior to FTIR. The FTIR sample is prepared by grounding thoroughly SWNT with potassium bromide (KBr) at 1-2 wt % and the resulting powder is pressed into a transparent pellet using hydraulic press. A plurality of fluorescein labeled carbon nanotubes 12 is dried in a vacuum oven (−20 in. Hg) at 80° C. overnight prior to FTIR. The FTIR sample is prepared by first grounding thoroughly 1-2 wt % of KBr. Dry fluorescein labeled samples are then treated with dichloromethane and sonicated for 5 min. Thereafter, this solution is poured into grounded KBr and dried in an oven for 10 min. Upon completion, the samples are grounded and the resulting powder is pressed into a transparent pellet using a hydraulic press.

To further verify the functionality of the fluorescence labeling of a plurality of carbon nanotubes 12, and to characterize the electric field that is optionally required to guide the migration of a plurality of energy-releasing carbon nanotube transponder 10 labelled with fluorescein, the migration of these carbon nanotubes 12 is monitored through a 0.5% agarose gel producing a porosity similar to that of brain. To that end, four electrodes are arranged in a quadripolar configuration according to methods already known in the art. These four electrodes are constructed with platinum/iridium wires and contacts are attached to a polycarbonate culture dish lid in a cubic and a non-cubic, tetrad orientation. In a cubic orientation one pair of electrodes is directly facing a second pair of electrode so that the four electrodes form a perfect square onto the surface of the agarose gel. In a non-cubic orientation, only one electrode of a first pair of electrodes is directly facing a second electrode of the second pair of electrode so that the four electrodes do not form a perfect square onto the surface of the agarose gel but rather form a diamond shape. 0.2 M sodium phosphate and 0.1 M citric acid buffer (Sigma Aldrich) at pH 6.0 are used to prepare a 0.5% agarose Type VII (Sigma Aldrich) gel. The electrode copper tips are placed at a depth of 8 mm in a 10 mm thick 0.5% agarose gel perpendicular to the gel surface prior to gel curing. Prior to gel curing injection loading wells are made by placing a 10 µl pipette tip in the gel. Two wells are created adjacent to two neighboring electrodes of a first pair of electrodes, and a third well is made equidistant between the two electrodes of the opposite second pair of electrodes. The stainless steel endings are connected to a constant current unit (Grass Technologies, West Warwick, R.I.). This setup is connected to a stimulus isolation unit (Grass Technologies) which in turn is controlled by an S88 stimulator (Grass Technologies). The charge of each electrode is opposite of the adjacent electrode arranged in an alternating manner. 1.5 µl of fluorescein labeled carbon nanotubes 12 or 1.5 µl of a plurality of energy-releasing carbon nanotube transponder 10 labelled with fluorescein is injected into the previously prepared agarose gel wells, in the well equidistant from the two electrodes. 0.2 M sodium phosphate and 0.1 M citric acid buffer at pH 6 are then injected on the gel surface to equalize the charge distribution and cool the gel.

With electrodes in a cubic orientation, an alternating (AC) electric field is applied for 3 h with the parameters 100 V, 5 mA, 1 Hz, 10 ms pulse width. In parallel, a control without electric field is prepared in the same manner.

With electrodes in a non-cubic orientation, an alternating (AC) electric field is applied for 3 h with the parameters 100 V, 5 mA, 1 Hz, however, a charge imbalance is introduced by applying two electric fields with two different pulse widths. One first pair of adjacent electrodes receives a pulse field of 50 ms while the second pair of electrodes receives a pulse field of 10 ms. In this non-cubic configuration, the well where the injection takes place, equidistant from the two electrodes, receives a pulse field of 50 ms. The fluorescence of this seventh exemplary embodiment is visualized using a Blue View Transilluminator (Vernier, Beaverton, Oreg.). This exemplary embodiment allows for the characterization of a biocompatible electric field that is delivered in a human brain tissue to optionally guide the migration of the energy-releasing carbon nanotube transponder 10. According to this exemplary embodiment, a preferred electrode configuration in vitro as well as in vivo is a quadripolar configuration that allows for the controlled migration of a plurality of carbon nanotube transponder 10 through the electric field generated between the four electrodes. Methods already known in the art allow for the direct transition from in vitro to in vivo settings with little modifications. In vivo, the energy-releasing carbon nanotube transponder 10 is preferentially labeled with technetium (99mTc), a molecular label 22, as exemplified in example 6.

The invention claimed is:

1. An energy-releasing carbon nanotube transponder responsive to changes in a chemical concentration or electrical property of its environment, and wherein said energy-releasing carbon nanotube transponder is up to 500 nanometers in diameter for delivering electrical energy to a cellular tissue, the energy-releasing carbon nanotube transponder comprising:
   (a) at least one carbon nanotube; and
   (b) a nanocapacitor connected to a first end of said at least one carbon nanotube, wherein said nanocapacitor is capable of storing a predetermined amount of electric energy, and said at least one carbon nanotube being connected to said nanocapacitor acts as a nanoswitch for releasing said predetermined amount of electrical energy to said cellular tissue in response to a change in the environment of said energy-releasing carbon nanotube transponder, and wherein a plurality of said energy-releasing carbon nanotube transponders is capable of releasing a biologically non-destructive electric charge in the range of between about 4 and about 20 microCoulombs/cm$^2$ to said cellular tissue.

2. The energy-releasing carbon nanotube transponder according to claim 1, further comprising a coiled nanowire located inside said nanocapacitor.

3. The energy-releasing carbon nanotube transponder according to claim 1, further comprising a coiled nanowire located outside said nanocapacitor.

4. The energy-releasing carbon nanotube transponder according to claim 1, further comprising a biocompatible coating on the outer surface of said energy-releasing carbon nanotube transponder.

5. The energy-releasing carbon nanotube transponder according to claim 4, wherein said biocompatible coating is a material selected from the group consisting of polylactic acid (PLA), polyglycolic acid (PGA), poly lactide co-glycolide (PLGA) and chitosan.

6. The energy-releasing carbon nanotube transponder according to claim 1, further comprising a molecular label linked to a free end of at least one said carbon nanotube, the free end of said carbon nanotube being distal from said nanocapacitor.

7. The energy-releasing carbon nanotube transponder according to claim 6, wherein said molecular label is a material selected from the group consisting of technetium and indium-111.

8. The energy-releasing carbon nanotube transponder according to claim 1, further comprising a biomolecule ligand linked to a free end of at least one said carbon nanotube, the free end of said carbon nanotube being distal from said nanocapacitor.

9. The energy-releasing carbon nanotube transponder according to claim 8, wherein said biomolecule ligand is Interleukin-13 (IL-13) or glutamate.

10. The energy-releasing carbon nanotube transponder according to claim 8 in which the binding of said biomolecule ligand to a cellular receptor changes an electronic characteristic of said carbon nanotube, and wherein a modification of said electronic characteristic induces the release of the electrical energy stored in said nanocapacitor into the environment of said energy-releasing carbon nanotube transponder through said carbon nanotube that acts as a nanowire.

11. The energy-releasing carbon nanotube transponder according to claim 1, in which changes in said chemical concentration in the environment of said energy-releasing carbon nanotube transponder modify an electronic characteristic of said carbon nanotube, and wherein a modification of said electronic characteristic induces the release of the electrical energy stored in said nanocapacitor into the environment of said energy-releasing carbon nanotube transponder through said carbon nanotube that acts as a nanowire.

12. The energy-releasing carbon nanotube transponder according to claim 1, in which said chemical concentration is glutamate concentration or hydrogen ion concentration.

13. The energy-releasing carbon nanotube transponder according to claim 1, in which changes in said electrical property in the environment of said energy-releasing carbon nanotube transponder modify an electronic characteristic of said carbon nanotube, and wherein a modification of said electronic characteristic induces the release of the electrical energy stored in said nanocapacitor into the environment of said energy-releasing carbon nanotube transponder through said carbon nanotube that acts as a nanowire.

14. A method of using a plurality of energy-releasing carbon nanotube transponders to treat target cells in human and non-human patients by delivering a biologically non-destructive electric charge, the method comprising:
   (a) identifying target cells to be treated;
   (b) connecting at least one said nanosensor to a nanocapacitor to form an energy-releasing carbon nanotube transponder;
   (c) determining an electric charge to be provided to each nanocapacitor for a plurality of the energy-releasing carbon nanotube transponders to deliver a biologically non-destructive electric charge to the target cells in a range of between about 4 and about 20 microCoulombs/cm$^2$;
   (d) storing said electric charge into each nanocapacitor of the plurality of the energy-releasing carbon nanotube transponders;
   (e) placing the plurality of said energy-releasing carbon nanotube transponders proximate to the target cells; and
   (f) automatically releasing the electric charge from the nanocapacitor proximate to the target cells in response to an environmental stimulus.

15. The method according to claim 14, releasing the electric charge from the nanocapacitor proximate to the target cells in response to the environmental stimulus selected from the group consisting of binding of a biomolecule ligand onto its receptor located on the surface of the target cells; a change in ion concentration; a change in chemical concentration; and a change in an electrical field surrounding the energy-releasing carbon nanotube transponders.

16. The method according to claim 14, further comprising assessing treatment efficacy with the plurality of energy-releasing carbon nanotube transponders.

17. The method according to claim 14, further comprising determining a marker corresponding to the target cells.

18. The method according to claim 14, comprising identifying the target cells to be treated selected from the group consisting of cancer cells; cells responsible for epilepsy; cells responsible for alteration in the electrical conduction system of the heart and cells responsible for brain seizures.

19. The method according to claim 14, further comprising:
  (a) binding a molecular label selected from the group consisting of technetium and indium-111 to the energy-releasing carbon nanotube transponder; and
  (b) tracking the energy-releasing carbon nanotube transponder by detecting said molecular label.

20. The method according to claim 14, further comprising coating the outer surface of the energy-releasing carbon nanotube transponder with a biocompatible coating selected from the group consisting of polylactic acid (PLA), polyglycolic acid (PGA), poly lactide co-glycolide (PLGA) and chitosan.

21. The method according to claim 14, further comprising recharging each said nanocapacitor within said plurality of energy-releasing carbon nanotube transponders for allowing multiple treatments.

22. The method according to claim 14, further comprising guiding said plurality of energy-releasing carbon nanotube transponders through an electric field.

* * * * *